(12) United States Patent
Weber et al.

(10) Patent No.: US 10,017,745 B2
(45) Date of Patent: Jul. 10, 2018

(54) HYBRIDOMA CELL LINES (MY-C-CC0C2-259-1 A4) AND USE THEREOF FOR PRODUCING A MONOCLONAL ANTIBODY AGAINST HUMAN CARDIAC MYOSIN BINDING PROTEIN C (C-PROTEIN, MYBPC3, CMYBP-C OR MY-C)

(71) Applicant: Martin-Luther-Universitaet Halle-Wittenberg, Halle (Saale) (DE)

(72) Inventors: Ekkehard Weber, Halle (DE); Rita Medek, Halle (DE)

(73) Assignee: Martin-Luther-Universitaet Halle-Wittenber, Halle/Saale (DE)

( * ) Notice: Subject to any disclaimer, the term of this patent is extended or adjusted under 35 U.S.C. 154(b) by 0 days.

(21) Appl. No.: 15/114,670

(22) PCT Filed: Jan. 23, 2015

(86) PCT No.: PCT/DE2015/000028
§ 371 (c)(1),
(2) Date: Oct. 24, 2016

(87) PCT Pub. No.: WO2015/110114
PCT Pub. Date: Jul. 30, 2015

(65) Prior Publication Data
US 2017/0044501 A1    Feb. 16, 2017

(30) Foreign Application Priority Data

Jan. 27, 2014  (DE) .................. 10 2014 000 856

(51) Int. Cl.
*C07K 16/18*  (2006.01)
*C12N 5/16*  (2006.01)
*G01N 33/577*  (2006.01)

(52) U.S. Cl.
CPC ............. *C12N 5/16* (2013.01); *C07K 16/18* (2013.01); *G01N 33/577* (2013.01); *C07K 2317/14* (2013.01); *C07K 2317/34* (2013.01); *G01N 2333/4712* (2013.01)

(58) Field of Classification Search
CPC ........... C07K 2317/14; C07K 2317/34; C07K 16/14; C12N 5/16; G01N 2333/4712; G01N 33/577
See application file for complete search history.

(56) References Cited

U.S. PATENT DOCUMENTS 5,206,007 A    4/1993  Ooshima et al.

FOREIGN PATENT DOCUMENTS

EP    0435185 A1    7/1991
WO    2008104289 A1    9/2008

*Primary Examiner* — Tracy Vivlemore
*Assistant Examiner* — Carmencita M Belei
(74) *Attorney, Agent, or Firm* — Norris McLaughlin & Marcus, P.A.

(57) ABSTRACT

Monoclonal antibodies, which can be produced in vitro, against cardiac epitopes of the human My-C are produced by generating myeloma cell clones that produce such specific antibodies having epitope specificity. These monoclonal antibodies allow, among other things, the creation of an enzyme-linked immunosorbent assay (ELISA) for the specific, cross-reactivity-free quantitative determination of My-C in serum, plasma, whole blood or other body fluid. Specifically, a hybridoma cell clone producing a monoclonal antibody that detects and binds a cardiac epitope in the My-C is provided, which has no cross-reactivity with respect to the myosin-binding proteins of the skeletal muscles. The hybridoma cell line can be obtained by fusing myeloma cells with spleen cells of a test animal, in particular a mouse, immunized against recombinant My-C.

10 Claims, 5 Drawing Sheets

FIG. 1:

Primary structure of cardiac My-C in the region of the epitope (labeled) detected by the monoclonal antibody anti-My-C-cC0C2-259-1A4 compared to the primary structures of My-C of skeletal muscles and smooth muscles (MYC1_HUMAN and MYC2_HUMAN).

```
121
PAP AAELGESAPSPK GSSSAALNGPTPGAPDDPIGLFVMRPQDGEVTVGGSITFSARVAG
180 Q14896 MYC3_HUMAN

40              PEDQS       PT   AEEPTGVFLKKPDSVSVETGKDAVVVAKVNG
77 Q14324 MYC2_HUMAN

43              PGEEQ       AKQNANSQLSILFIEKPQGGTVKVGEDITFIAKVKA
83 Q00872 MYC1_HUMAN
```

FIG. 2:

Amino acid sequence of the cC0C2 domains of cardiad My-C (myosin-binding protein C)

```
  1  MPEPGKKPVS   AFSKKPRSVE   VAAGSPAVFE   AETERAGVKV
 61  GTRHTLTVRE   VGPADQGSYA   VIAGSSKVKF   DLKVIEAEKA
121  PAPAAELGES   APSPKGSSSA   ALNGPTPGAP   DDPIGLFVMR
181  ASLLKPPVVK   WFKGKWVDLS   SKVGQHLQLH   DSYDRASKVY
241  VSTKDKFECS   NFNLTVHEAM   GTGDLDLLSA   FRRTSLAGGG
301  KRDSFRTPRD   SKLEAPAEED   VWEILRQAPP   SEYERIAFQY
361  KSTAFQKKLE   PAYQVSKGHK   IRLTVELADH   DAEVKWLKNG
421  LTISQCSLAD   DAAYQCVVGG   EKCSTELFVK   E
```

FIG. 3:

Epitope mapping of anti-My-C-cC0C2-259-1A4

ECL film: detection of the monoclonal antibody 1A4 bound to spots 31 and 32 of the My-C-cC0C2 Pepspot membrane.

FIG. 4:

Epitope mapping: list of the overlapping 15-mer peptides present in the PepSpots 1 to 41 of the mapping membrane

| Spot | Start AA | Peptide Sequence | Peptide length | |
|---|---|---|---|---|
| 1 | 1 | MPEPGKKPVSAFSKK | 15 | |
| 2 | 5 | GKKPVSAFSKKPRSV | 15 | |
| 3 | 9 | VSAFSKKPRSVEVAA | 15 | |
| 4 | 13 | SKKPRSVEVAAGSPA | 15 | |
| 5 | 17 | RSVEVAAGSPAVFEA | 15 | |
| 6 | 21 | VAAGSPAVFEAETER | 15 | |
| 7 | 25 | SPAVFEAETERAGVK | 15 | |
| 8 | 29 | FEAETERAGVKVRWQ | 15 | |
| 9 | 33 | TERAGVKVRWQRGGS | 15 | |
| 10 | 37 | GVKVRWQRGGSDISA | 15 | |
| 11 | 41 | RWQRGGSDISASNKY | 15 | |
| 12 | 45 | GGSDISASNKYGLAT | 15 | |
| 13 | 49 | ISASNKYGLATEGTR | 15 | |
| 14 | 53 | NKYGLATEGTRHTLT | 15 | |
| 15 | 57 | LATEGTRHTLTVREV | 15 | |
| 16 | 61 | GTRHTLTVREVGPAD | 15 | |
| 17 | 65 | TLTVREVGPADQGSY | 15 | |
| 18 | 69 | REVGPADQGSYAVIA | 15 | |
| 19 | 73 | PADQGSYAVIAGSSK | 15 | |
| 20 | 77 | GSYAVIAGSSKVKFD | 15 | |
| 21 | 81 | VIAGSSKVKFDLKVI | 15 | |
| 22 | 85 | SSKVKFDLKVIEAEK | 15 | |
| 23 | 89 | KFDLKVIEAEKAEPM | 15 | |
| 24 | 93 | KVIEAEKAEPMLAPA | 15 | |
| 25 | 97 | AEKAEPMLAPAPAPA | 15 | |
| 26 | 101 | EPMLAPAPAPAEATG | 15 | |
| 27 | 105 | APAPAPAEATGAPGE | 15 | |
| 28 | 109 | APAEATGAPGEAPAP | 15 | |
| 29 | 113 | ATGAPGEAPAPAAEL | 15 | |
| 30 | 117 | PGEAPAPAAELGESA | 15 | |
| 31 | 121 | PAPAAELGESAPSPK | 15 | 1A4 |
| 32 | 125 | AELGESAPSPKGSSS | 15 | 1A4 |
| 33 | 129 | ESAPSPKGSSSAALN | 15 | |
| 34 | 133 | SPKGSSSAALNGPTP | 15 | |
| 35 | 137 | SSSAALNGPTPGAPD | 15 | |
| 36 | 141 | ALNGPTPGAPDPIG | 15 | |
| 37 | 145 | PTPGAPDPIGLFVM | 15 | |
| 38 | 149 | APDPIGLFVMRPQD | 15 | |
| 39 | 153 | PIGLFVMRPQDGEVT | 15 | |
| 40 | 157 | FVMRPQDGEVTVGGS | 15 | |
| 41 | 161 | PQDGEVTVGGSITFS | 15 | |

FIG. 5:

Proof of binding of the monoclonal antibody anti-My-C-cC0C2-259-1A4 to recombinant cC0C2 in the ELISA.

Creation of the ELISA.

cC0C2 detection:

a:  Adsorbed antigen: 50 µl cC0C2 (2 µg/ml) per well
   + cC0C2-259-1A4 (purified, 0.4 mg/ml)
   + secondary anti-mouse-IgG, POD-labeled, 1:5000
   + ABTS Control:

b:  Adsorbed antigen: 50 µl cC0C2 (2 µg/ml) per well
   + secondary anti-mouse-IgG, POD-labeled, 1:5000
   + ABTS Measurement:

Absorption at 405 nm

Series A (a): dilution of the purified antibody (0.4 mg/ml) 1:10 -> 1:20000

Series B (b): control

_US 10,017,745 B2_

SEQUENCE LISTING

<160> NUMBER OF SEQ ID NOS: 46

<210> SEQ ID NO 1
<211> LENGTH: 12
<212> TYPE: PRT
<213> ORGANISM: Human

<400> SEQUENCE: 1

Ala Ala Glu Leu Gly Glu Ser Ala Pro Ser Pro Lys
1               5                   10

<210> SEQ ID NO 2
<211> LENGTH: 60
<212> TYPE: PRT
<213> ORGANISM: Human

<400> SEQUENCE: 2

Pro Ala Pro Ala Ala Glu Leu Gly Glu Ser Ala Pro Ser Pro Lys Gly
1               5                   10                  15

Ser Ser Ser Ala Ala Leu Asn Gly Pro Thr Pro Gly Ala Pro Asp Asp
                20                  25                  30

Pro Ile Gly Leu Phe Val Met Arg Pro Gln Asp Gly Glu Val Thr Val
            35                  40                  45

Gly Gly Ser Ile Thr Phe Ser Ala Arg Val Ala Gly
        50                  55                  60

<210> SEQ ID NO 3
<211> LENGTH: 38
<212> TYPE: PRT
<213> ORGANISM: Human

<400> SEQUENCE: 3

Pro Glu Asp Gln Ser Pro Thr Ala Glu Glu Pro Thr Gly Val Phe Leu
1               5                   10                  15

Lys Lys Pro Asp Ser Val Ser Val Gly Thr Gly Lys Asp Ala Val Val
                20                  25                  30

Val Ala Lys Val Asn Gly
        35

<210> SEQ ID NO 4
<211> LENGTH: 41
<212> TYPE: PRT
<213> ORGANISM: Human

<400> SEQUENCE: 4

Pro Gly Glu Glu Gln Ala Lys Gln Asn Ala Asn Ser Gln Leu Ser Ile
1               5                   10                  15

Leu Phe Ile Glu Lys Pro Gln Gly Gly Thr Val Lys Val Gly Glu Asp
                20                  25                  30

Ile Thr Phe Ile Ala Lys Val Lys Ala
        35                  40

<210> SEQ ID NO 5
<211> LENGTH: 311
<212> TYPE: PRT
<213> ORGANISM: Human

<400> SEQUENCE: 5

Met Pro Glu Pro Gly Lys Lys Pro Val Ser Ala Phe Ser Lys Lys Pro
1               5                   10                  15

Arg Ser Val Glu Val Ala Ala Gly Ser Pro Ala Val Phe Glu Ala Glu

```
                  20                  25                  30
        Thr Glu Arg Ala Gly Val Lys Val Gly Thr Arg His Thr Leu Thr Val
                         35                  40                  45

Arg Glu Val Gly Pro Ala Asp Gln Gly Ser Tyr Ala Val Ile Ala Gly
         50                  55                  60

Ser Ser Lys Val Lys Phe Asp Leu Lys Val Ile Glu Ala Glu Lys Ala
         65                  70                  75                  80

Pro Ala Pro Ala Ala Glu Leu Gly Glu Ser Ala Pro Ser Pro Lys Gly
                         85                  90                  95

Ser Ser Ser Ala Ala Leu Asn Gly Pro Thr Pro Gly Ala Pro Asp Asp
                    100                 105                 110

Pro Ile Gly Leu Phe Val Met Arg Ala Ser Leu Leu Lys Pro Pro Val
                    115                 120                 125

Val Lys Trp Phe Lys Gly Lys Trp Val Asp Leu Ser Ser Lys Val Gly
                    130                 135                 140

Gln His Leu Gln Leu His Asp Ser Tyr Asp Arg Ala Ser Lys Val Tyr
        145                 150                 155                 160

Val Ser Thr Lys Asp Lys Phe Glu Cys Ser Asn Phe Asn Leu Thr Val
                        165                 170                 175

His Glu Ala Met Gly Thr Gly Asp Leu Asp Leu Leu Ser Ala Phe Arg
                        180                 185                 190

Arg Thr Ser Leu Ala Gly Gly Gly Lys Arg Asp Ser Phe Arg Thr Pro
                        195                 200                 205

Arg Asp Ser Lys Leu Glu Ala Pro Ala Glu Glu Asp Val Trp Glu Ile
                        210                 215                 220

Leu Arg Gln Ala Pro Pro Ser Glu Tyr Glu Arg Ile Ala Phe Gln Tyr
        225                 230                 235                 240

Lys Ser Thr Ala Phe Gln Lys Lys Leu Glu Pro Ala Tyr Gln Val Ser
                        245                 250                 255

Lys Gly His Lys Ile Arg Leu Thr Val Glu Leu Ala Asp His Asp Ala
                        260                 265                 270

Glu Val Lys Trp Leu Lys Asn Gly Leu Thr Ile Ser Gln Cys Ser Leu
                        275                 280                 285

Ala Asp Asp Ala Ala Tyr Gln Cys Val Val Gly Gly Glu Lys Cys Ser
                        290                 295                 300

Thr Glu Leu Phe Val Lys Glu
        305                 310

<210> SEQ ID NO 6
<211> LENGTH: 15
<212> TYPE: PRT
<213> ORGANISM: Human

<400> SEQUENCE: 6

Met Pro Glu Pro Gly Lys Lys Pro Val Ser Ala Phe Ser Lys Lys
1               5                   10                  15

<210> SEQ ID NO 7
<211> LENGTH: 15
<212> TYPE: PRT
<213> ORGANISM: Human

<400> SEQUENCE: 7

Gly Lys Lys Pro Val Ser Ala Phe Ser Lys Lys Pro Arg Ser Val
1               5                   10                  15
```

```
<210> SEQ ID NO 8
<211> LENGTH: 15
<212> TYPE: PRT
<213> ORGANISM: Human

<400> SEQUENCE: 8

Val Ser Ala Phe Ser Lys Lys Pro Arg Ser Val Glu Val Ala Ala
1               5                   10                  15

<210> SEQ ID NO 9
<211> LENGTH: 15
<212> TYPE: PRT
<213> ORGANISM: Human

<400> SEQUENCE: 9

Ser Lys Lys Pro Arg Ser Val Glu Val Ala Ala Gly Ser Pro Ala
1               5                   10                  15

<210> SEQ ID NO 10
<211> LENGTH: 15
<212> TYPE: PRT
<213> ORGANISM: Human

<400> SEQUENCE: 10

Arg Ser Val Glu Val Ala Ala Gly Ser Pro Ala Val Phe Glu Ala
1               5                   10                  15

<210> SEQ ID NO 11
<211> LENGTH: 15
<212> TYPE: PRT
<213> ORGANISM: Human

<400> SEQUENCE: 11

Val Ala Ala Gly Ser Pro Ala Val Phe Glu Ala Glu Thr Glu Arg
1               5                   10                  15

<210> SEQ ID NO 12
<211> LENGTH: 15
<212> TYPE: PRT
<213> ORGANISM: Human

<400> SEQUENCE: 12

Ser Pro Ala Val Phe Glu Ala Glu Thr Glu Arg Ala Gly Val Lys
1               5                   10                  15

<210> SEQ ID NO 13
<211> LENGTH: 15
<212> TYPE: PRT
<213> ORGANISM: Human

<400> SEQUENCE: 13

Phe Glu Ala Glu Thr Glu Arg Ala Gly Val Lys Val Arg Trp Gln
1               5                   10                  15

<210> SEQ ID NO 14
<211> LENGTH: 15
<212> TYPE: PRT
<213> ORGANISM: Human

<400> SEQUENCE: 14

Thr Glu Arg Ala Gly Val Lys Val Arg Trp Gln Arg Gly Gly Ser
1               5                   10                  15

<210> SEQ ID NO 15
<211> LENGTH: 15
```

```
<212> TYPE: PRT
<213> ORGANISM: Human

<400> SEQUENCE: 15

Gly Val Lys Val Arg Trp Gln Arg Gly Gly Ser Asp Ile Ser Ala
1               5                   10                  15

<210> SEQ ID NO 16
<211> LENGTH: 15
<212> TYPE: PRT
<213> ORGANISM: Human

<400> SEQUENCE: 16

Arg Trp Gln Arg Gly Gly Ser Asp Ile Ser Ala Ser Asn Lys Tyr
1               5                   10                  15

<210> SEQ ID NO 17
<211> LENGTH: 15
<212> TYPE: PRT
<213> ORGANISM: Human

<400> SEQUENCE: 17

Gly Gly Ser Asp Ile Ser Ala Ser Asn Lys Tyr Gly Leu Ala Thr
1               5                   10                  15

<210> SEQ ID NO 18
<211> LENGTH: 15
<212> TYPE: PRT
<213> ORGANISM: Human

<400> SEQUENCE: 18

Ile Ser Ala Ser Asn Lys Tyr Gly Leu Ala Thr Glu Gly Thr Arg
1               5                   10                  15

<210> SEQ ID NO 19
<211> LENGTH: 15
<212> TYPE: PRT
<213> ORGANISM: Human

<400> SEQUENCE: 19

Asn Lys Tyr Gly Leu Ala Thr Glu Gly Thr Arg His Thr Leu Thr
1               5                   10                  15

<210> SEQ ID NO 20
<211> LENGTH: 15
<212> TYPE: PRT
<213> ORGANISM: Human

<400> SEQUENCE: 20

Leu Ala Thr Glu Gly Thr Arg His Thr Leu Thr Val Arg Glu Val
1               5                   10                  15

<210> SEQ ID NO 21
<211> LENGTH: 15
<212> TYPE: PRT
<213> ORGANISM: Human

<400> SEQUENCE: 21

Gly Thr Arg His Thr Leu Thr Val Arg Glu Val Gly Pro Ala Asp
1               5                   10                  15

<210> SEQ ID NO 22
<211> LENGTH: 15
<212> TYPE: PRT
<213> ORGANISM: Human
```

<400> SEQUENCE: 22

Thr Leu Thr Val Arg Glu Val Gly Pro Ala Asp Gln Gly Ser Tyr
1               5                   10                  15

<210> SEQ ID NO 23
<211> LENGTH: 15
<212> TYPE: PRT
<213> ORGANISM: Human

<400> SEQUENCE: 23

Arg Glu Val Gly Pro Ala Asp Gln Gly Ser Tyr Ala Val Ile Ala
1               5                   10                  15

<210> SEQ ID NO 24
<211> LENGTH: 15
<212> TYPE: PRT
<213> ORGANISM: Human

<400> SEQUENCE: 24

Pro Ala Asp Gln Gly Ser Tyr Ala Val Ile Ala Gly Ser Ser Lys
1               5                   10                  15

<210> SEQ ID NO 25
<211> LENGTH: 15
<212> TYPE: PRT
<213> ORGANISM: Human

<400> SEQUENCE: 25

Gly Ser Tyr Ala Val Ile Ala Gly Ser Ser Lys Val Lys Phe Asp
1               5                   10                  15

<210> SEQ ID NO 26
<211> LENGTH: 15
<212> TYPE: PRT
<213> ORGANISM: Human

<400> SEQUENCE: 26

Val Ile Ala Gly Ser Ser Lys Val Lys Phe Asp Leu Lys Val Ile
1               5                   10                  15

<210> SEQ ID NO 27
<211> LENGTH: 15
<212> TYPE: PRT
<213> ORGANISM: Human

<400> SEQUENCE: 27

Ser Ser Lys Val Lys Phe Asp Leu Lys Val Ile Glu Ala Glu Lys
1               5                   10                  15

<210> SEQ ID NO 28
<211> LENGTH: 15
<212> TYPE: PRT
<213> ORGANISM: Human

<400> SEQUENCE: 28

Lys Phe Asp Leu Lys Val Ile Glu Ala Glu Lys Ala Glu Pro Met
1               5                   10                  15

<210> SEQ ID NO 29
<211> LENGTH: 15
<212> TYPE: PRT
<213> ORGANISM: Human

<400> SEQUENCE: 29

```
Lys Val Ile Glu Ala Glu Lys Ala Glu Pro Met Leu Ala Pro Ala
1               5                   10                  15
```

<210> SEQ ID NO 30
<211> LENGTH: 15
<212> TYPE: PRT
<213> ORGANISM: Human

<400> SEQUENCE: 30

```
Ala Glu Lys Ala Glu Pro Met Leu Ala Pro Ala Pro Ala Pro Ala
1               5                   10                  15
```

<210> SEQ ID NO 31
<211> LENGTH: 15
<212> TYPE: PRT
<213> ORGANISM: Human

<400> SEQUENCE: 31

```
Glu Pro Met Leu Ala Pro Ala Pro Ala Pro Ala Glu Ala Thr Gly
1               5                   10                  15
```

<210> SEQ ID NO 32
<211> LENGTH: 15
<212> TYPE: PRT
<213> ORGANISM: Human

<400> SEQUENCE: 32

```
Ala Pro Ala Pro Ala Pro Ala Glu Ala Thr Gly Ala Pro Gly Glu
1               5                   10                  15
```

<210> SEQ ID NO 33
<211> LENGTH: 15
<212> TYPE: PRT
<213> ORGANISM: Human

<400> SEQUENCE: 33

```
Ala Pro Ala Glu Ala Thr Gly Ala Pro Gly Glu Ala Pro Ala Pro
1               5                   10                  15
```

<210> SEQ ID NO 34
<211> LENGTH: 15
<212> TYPE: PRT
<213> ORGANISM: Human

<400> SEQUENCE: 34

```
Ala Thr Gly Ala Pro Gly Glu Ala Pro Ala Pro Ala Ala Glu Leu
1               5                   10                  15
```

<210> SEQ ID NO 35
<211> LENGTH: 15
<212> TYPE: PRT
<213> ORGANISM: Human

<400> SEQUENCE: 35

```
Pro Gly Glu Ala Pro Ala Pro Ala Ala Glu Leu Gly Glu Ser Ala
1               5                   10                  15
```

<210> SEQ ID NO 36
<211> LENGTH: 15
<212> TYPE: PRT
<213> ORGANISM: Human

<400> SEQUENCE: 36

```
Pro Ala Pro Ala Ala Glu Leu Gly Glu Ser Ala Pro Ser Pro Lys
```

-continued

```
1               5                   10                  15
```

<210> SEQ ID NO 37
<211> LENGTH: 15
<212> TYPE: PRT
<213> ORGANISM: Human

<400> SEQUENCE: 37

```
Ala Glu Leu Gly Glu Ser Ala Pro Ser Pro Lys Gly Ser Ser Ser
1               5                   10                  15
```

<210> SEQ ID NO 38
<211> LENGTH: 15
<212> TYPE: PRT
<213> ORGANISM: Human

<400> SEQUENCE: 38

```
Glu Ser Ala Pro Ser Pro Lys Gly Ser Ser Ser Ala Ala Leu Asn
1               5                   10                  15
```

<210> SEQ ID NO 39
<211> LENGTH: 15
<212> TYPE: PRT
<213> ORGANISM: Human

<400> SEQUENCE: 39

```
Ser Pro Lys Gly Ser Ser Ser Ala Ala Leu Asn Gly Pro Thr Pro
1               5                   10                  15
```

<210> SEQ ID NO 40
<211> LENGTH: 15
<212> TYPE: PRT
<213> ORGANISM: Human

<400> SEQUENCE: 40

```
Ser Ser Ser Ala Ala Leu Asn Gly Pro Thr Pro Gly Ala Pro Asp
1               5                   10                  15
```

<210> SEQ ID NO 41
<211> LENGTH: 15
<212> TYPE: PRT
<213> ORGANISM: Human

<400> SEQUENCE: 41

```
Ala Leu Asn Gly Pro Thr Pro Gly Ala Pro Asp Asp Pro Ile Gly
1               5                   10                  15
```

<210> SEQ ID NO 42
<211> LENGTH: 15
<212> TYPE: PRT
<213> ORGANISM: Human

<400> SEQUENCE: 42

```
Pro Thr Pro Gly Ala Pro Asp Asp Pro Ile Gly Leu Phe Val Met
1               5                   10                  15
```

<210> SEQ ID NO 43
<211> LENGTH: 15
<212> TYPE: PRT
<213> ORGANISM: Human

<400> SEQUENCE: 43

```
Ala Pro Asp Asp Pro Ile Gly Leu Phe Val Met Arg Pro Gln Asp
1               5                   10                  15
```

```
<210> SEQ ID NO 44
<211> LENGTH: 15
<212> TYPE: PRT
<213> ORGANISM: Human

<400> SEQUENCE: 44

Pro Ile Gly Leu Phe Val Met Arg Pro Gln Asp Gly Glu Val Thr
1               5                   10                  15

<210> SEQ ID NO 45
<211> LENGTH: 15
<212> TYPE: PRT
<213> ORGANISM: Human

<400> SEQUENCE: 45

Phe Val Met Arg Pro Gln Asp Gly Glu Val Thr Val Gly Gly Ser
1               5                   10                  15

<210> SEQ ID NO 46
<211> LENGTH: 15
<212> TYPE: PRT
<213> ORGANISM: Human

<400> SEQUENCE: 46

Pro Gln Asp Gly Glu Val Thr Val Gly Gly Ser Ile Thr Phe Ser
1               5                   10                  15
```

HYBRIDOMA CELL LINES (MY-C-CC0C2-259-1 A4) AND USE THEREOF FOR PRODUCING A MONOCLONAL ANTIBODY AGAINST HUMAN CARDIAC MYOSIN BINDING PROTEIN C (C-PROTEIN, MYBPC3, CMYBP-C OR MY-C)

BACKGROUND OF THE INVENTION

The invention relates to a mouse hybridoma clone producing a monoclonal antibody (anti-My-C-cC0C2-259-1A4; IgG1, kappa), which is directed against the cardiac myosin-binding protein C (C-protein, MYBPC3, cMyBP-C or My-C) and detects the same, and which does not react with the closely related isomers of My-C from the skeletal muscles. This monoclonal antibody is suitable as a catcher antibody or as a detection antibody for creating an enzyme-linked immunosorbent assay (ELISA) for quantitatively determining My-C in serum, plasma, whole blood or other body fluids for the early diagnosis of cardiac infarctions. Within the scope of this diagnostic procedure, this can allow a considerably early treatment of myocardial infarctions.

Due to the acute life-threatening hazard, myocardial infarctions must be diagnosed quickly and distinguished from other causes of chest pain. [1]

Determining biomarkers of myocardial necroses has meanwhile become an essential component in the diagnosis of infarctions with suspected non-ST-elevation acute coronary syndromes (NSTE-ACSs) and is imperative for making a diagnosis in the corresponding clinical context. At present, cardiac troponins (cTn) are considered the crucial biomarker. They are an integral component of the general infarction definition. [2] Cardiac troponins (cTn), however, have disadvantages, and new biomarkers could prove to be very valuable. [3]

The cTn concentration in the serum reaches a maximum only 16 to 18 hours after the onset of symptoms, and one disadvantage of the existing cTn tests is the lack of analytical sensitivity for detecting low cTn concentrations in the first hours after symptoms begin to manifest. [4; 5]

More recent cTn tests strive for a reliable determination of low cTn values; however, the reduced specificity thereof with respect to infarctions lowers the value thereof, since cTn concentrations in the vicinity of the 99th percentile of healthy test subjects can be observed.

However, even then the cTn concentrations are below this threshold in as many as 25% of the infarction patients. [6]

In view of the limited sensitivity and specificity of the cTn tests, corresponding guidelines (NICE) recommend determining the cTn 10 to 12 hours after the onset of symptoms (pain in the thoracic region) so as to confirm the diagnosis. [1]

While a number of biomarkers exist that are released more quickly after an infarction, none of these have prevailed, since these are not expressed in a cardioselective manner. [7] For this reason, current efforts are focused on analyzing the extent of the changes in the cTn concentrations over time so as to improve the validity of the cTn tests. It remains unclear how large the absolute difference in concentration would have to be to render differences in the analytical and biological variations of the cTn concentrations irrelevant for making the intended diagnosis.

The ideal biomarker would have to be released quickly from the myocardium after an infarction, but, contrary to comparable existing markers, would have to be a cardiac marker. The cardiac myosin-binding protein C (C-protein, MYBPC3, cMyBP-C or My-C) is a protein that meets these criteria. It was identified in the course of the proteomic analysis of coronary effluent from ischemic mouse hearts. [8] It is one of the most highly expressed proteins in the myocardium (19th out of 2,300 proteins), and the concentration is at least double that of cTnI and cTnT (92nd and 118th, respectively, out of 2,300 proteins). [9]

Figure 1:
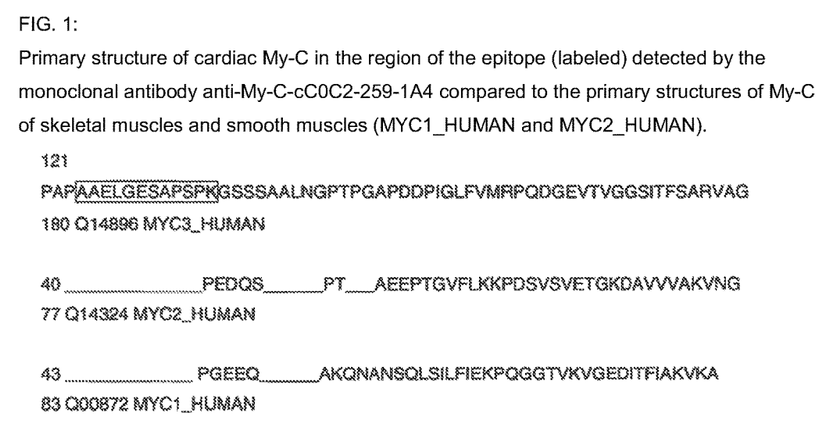
FIG. 1 shows the primary structure of cardiac My-C in the region of the epitope detected by the monoclonal antibody anti-My-C-cC0C2-259-1A4 (SEQ ID NO. 2) compared to the primary structures of My-C of skeletal muscles (sequence identified by MYC1 HUMAN (SEQ ID NO. 3)) and smooth muscles (sequence identified by MYC2 HUMAN (SEQ ID NO. 4))

Three different My-C isomers exist, which are encoded by different genes. In contrast with the My-C of the fast skeletal muscles and the My-C of the slow skeletal muscles, the cardiac isoform has a unique N-terminal domain (FIG. 1) and other cardiac regions that could serve as specific epitopes. [10]

The release of My-C after myocardial infarctions or damage has been demonstrated [8; 11; 12; 13; 14] and the progression of the increases in the concentration over time was compared to that of cTn.

SUMMARY OF THE INVENTION

It was the object of the invention to create monoclonal antibodies, which can be produced in vitro, against cardiac epitopes of the human My-C by generating myeloma cell clones that produce such specific antibodies having epitope specificity. These monoclonal antibodies were to allow, among other things, the creation of an enzyme-linked immunosorbent assay (ELISA) for the specific, cross-reactivity-free quantitative determination of My-C in serum, plasma, or whole blood or other body fluid.

The object is achieved by generating a hybridoma cell clone producing a monoclonal antibody that detects and binds a cardiac epitope in the My-C, and that has no cross-reactivity with respect to the myosin-binding proteins of the skeletal muscles. The hybridoma cell line can be obtained by fusing myeloma cells with spleen cells of a test animal, in particular a mouse, immunized against recombinant My-C. The hybridoma cell line was deposited on Dec. 10, 2013 with the DSMZ with accession number DSM ACC3224 in accordance with the requirements of the Budapest Treaty. The antibody produced by this hybridoma cell clone, in combination with one or more other monoclonal antibodies in an ELISA, is suitable for sensitively determining the concentration of My-C in the serum, and thus for the early diagnosis of cardiac infarctions.

The invention furthermore relates to epitope-specific antibodies produced by the hybridoma cell line, and to the use thereof.

Figure 2:
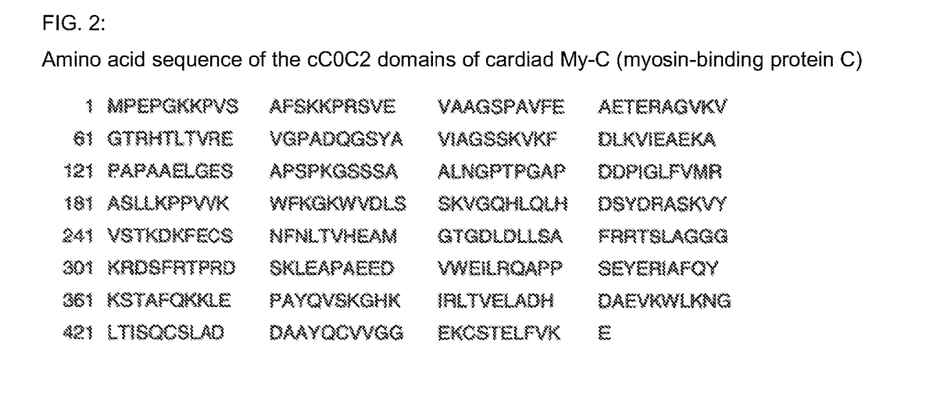
FIG. 2 shows the amino acid sequence of the cC0C2 domains of cardiac My-C (SEQ ID NO. 5)

So as to generate hybridoma clones producing monoclonal antibodies against human cardiac My-C, BALB/c mice were immunized in the known manner at intervals of six to eight weeks with the recombinant domains cC0C2 of the My-C; (FIG. 2). The mice received booster immunizations prior to having the spleen removed. The isolated spleen cells were fused in the known manner with cells from the mouse myeloma cell line P3X63Ag8.653 (ATCC CRL 1580) and were cultivated in suitable media. [15]

The hybridomas that exclusively produce antibodies against the human My-C are selected, cloned multiple times, and propagated. The primary selection of these specific hybridomas was carried out using an ELISA in which the C0C2 peptide of the My-C was adsorbed on the surface of microtiter plates.

The epitope specificity of the monoclonal antibody of the clone according to the invention selected from the clones based on these criteria was ascertained by way of peptide scanning (Pepscan) (16, 17, 18). For this purpose, peptides (having sequences identical to the cC0C2 domain of the My-C used for the immunization) having a length of 15 amino acid esters were synthesized as individual spots on a membrane. The sequences of the 15-mer peptides of neighboring spots overlap, so that the entire amino acid sequence of the cC0C2 domain of the My-C was synthesized so as to overlap in a total of 111 spots. These peptides were incubated on the mapping membrane using the monoclonal antibody according to the invention. The bound antibody was detected by way of the ECL™ (enhanced chemiluminescence) system on film.

Figure 3:
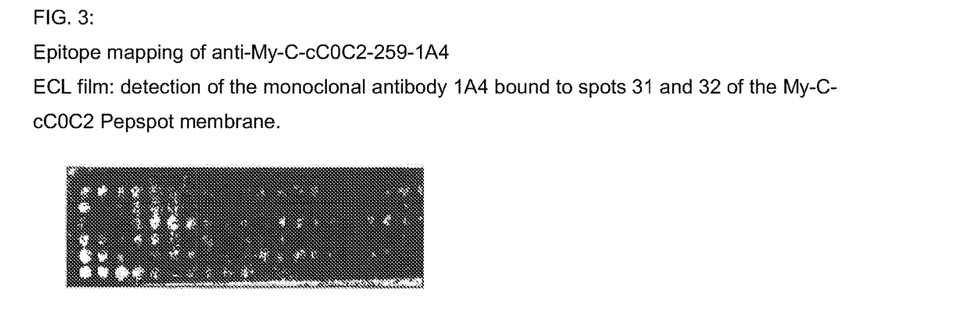
FIG. 3 shows epitope mapping of anti-My-C-cC02-259-1A4.
Figure 4:
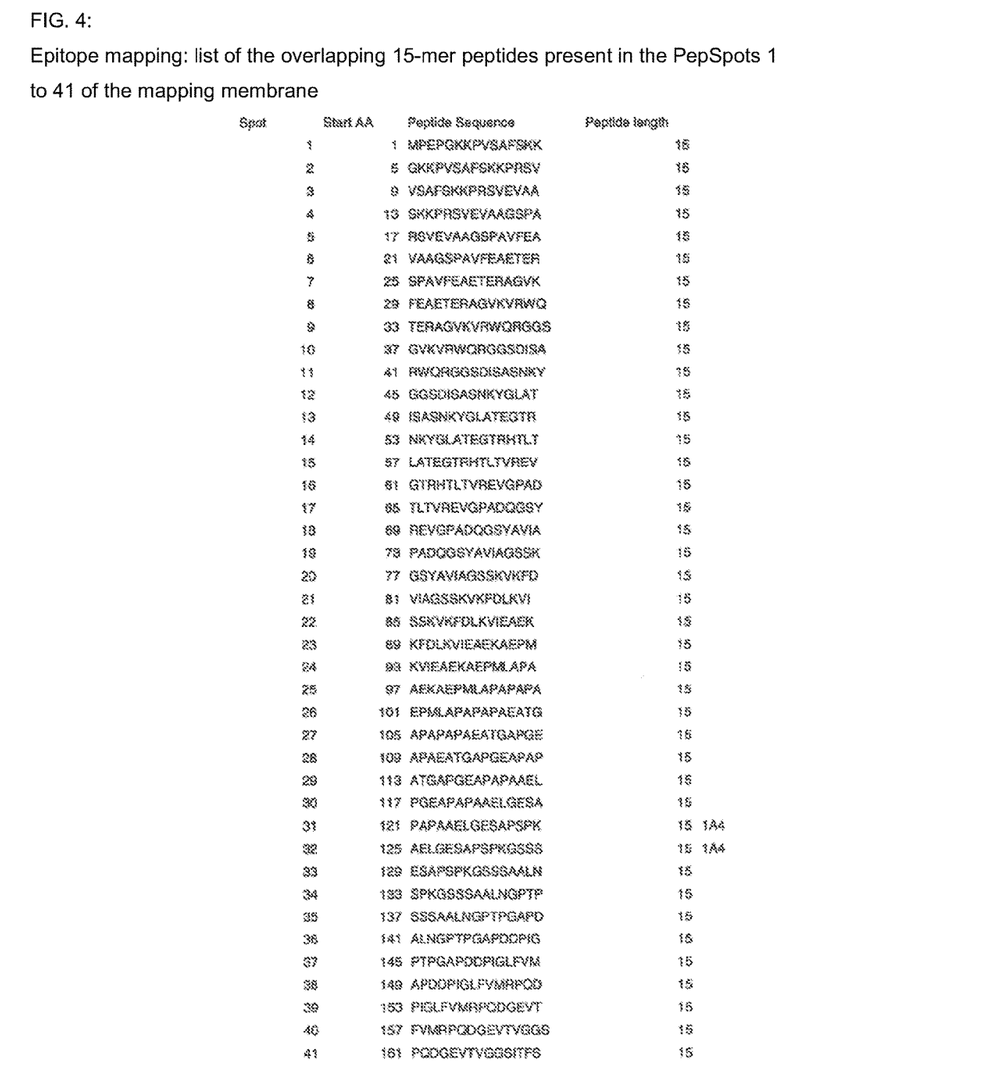
FIG. 4 shows epitope mapping, namely, a list of the peptides present in the overlapping 15-mer peptides present in the PepSpots 1 to 41 of the mapping membrane (Spots 1-41 correspond to SEQ ID NOs. 6-46, respectively)

This method allowed an ascertainment as to which of the 15-mer peptides are identified by the monoclonal antibody produced according to the invention. Using the known sequence of the peptides in the detected individual spots (see FIG. 3), it was possible to infer the amino acid sequence of the epitope of the human My-C identified by the monoclonal antibody of the hybridoma clone (FIG. 4).

The monoclonal antibody 1A4 produced by the hybridoma clone generated according to the invention binds in the human My-C to the epitope having the sequence $A_{124}$-A-E-L-G-E-S-A-P-S-P-K-(SEQ ID NO. 1)

Figure 5:
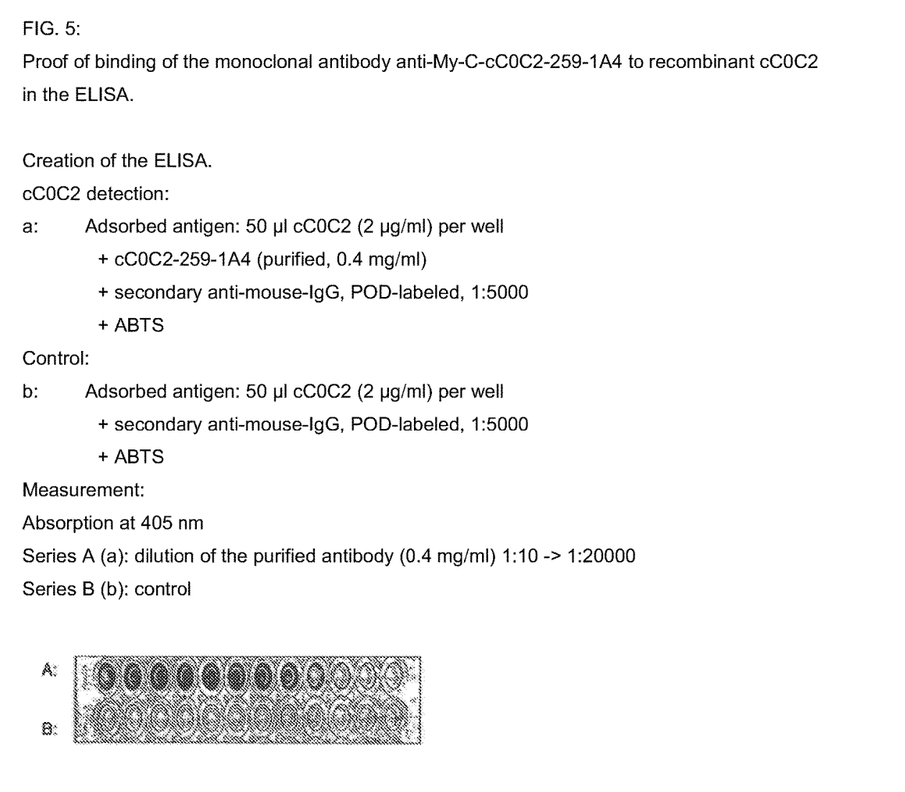
FIG. 5 shows proof of binding of the monoclonal antibody anti-My-C-cC0C2-259-1A4 to recombinant cC0C2 in the ELISA.

The proof that the monoclonal antibody produced according to the invention detects not only peptides on this PepSpot membrane, but also the entire molecule of the cC0C2 domain of the human My-C that includes this epitope was provided by the use thereof in the ELISA. Such an exemplary ELISA using the monoclonal antibody 1A4 is shown in FIG. 5.

The above-described, epitope-characterized monoclonal antibody ($IgG_1$, kappa) can be modified or labeled in the native form thereof, or in the form of a fragment. This antibody, or the modified forms thereof, can be used to clarify the processing of the human My-C, the kinetics of the release thereof and of the clearance thereof from the serum or other body fluid, for the qualitative detection thereof, and the quantitative determination thereof (such as ELISA and Western Blot), in immunohistology or as a diagnostic agent.

DETAILED DESCRIPTION OF THE INVENTION

The invention will be described in more detail hereafter by way of exemplary embodiments.

Exemplary Embodiments

EXAMPLE 1

Production of the Hybridoma Cell Line

The spleen of a mouse immunized in the known manner with cC0C2 of the My-C is removed under sterile conditions, and the spleen cells are flushed out of the spleen capsule using RPMI 1640 medium (LIFE TECHNOLOGIES™, Karlsruhe) with a syringe and isolated. The spleen cells are pelletized (10 minutes at 300.times.g), washed three times with RPMI 1640 medium, and resuspended in RPMI 1640 medium. They are then fused with myeloma cells of the line P3X63Ag8.653 (ATTC CRL 1580). For this purpose, cultivated myeloma cells, which are in the log phase of growth, are likewise pelletized and washed three times. $1 \times 10^8$ spleen cells and $5 \times 10^7$ myeloma cells are pipetted into a centrifuge tube, mixed intensively and centrifuged; 1.5 ml preheated 50% polyethylene glycol 1500 (Roche, Basel) is added dropwise to the cell sediment within one minute, while the tubule is continuously rotated at 37° C. The fusion batch is then incubated for another minute at 37° C. In the following three minutes, preheated medium (RPMI 1640) is added dropwise, 1 ml being added in the first minute, 3 ml in the second minute, and then 18 ml. Centrifuging is carried out immediately thereafter at 200×g for 10 minutes. The cell pellet is placed in RPMI 1640 medium comprising 10% FCS and HAT. A portion of the pellets are seeded in 96-well culture plates, and the remainder is frozen in liquid nitrogen at −196° C. Mouse peritoneal macrophages, which were cultivated 1 day prior to the fusion ($1 \times 10^4$ macrophages per well in HAT medium), are used as feeder cells during cultivation. The cells are incubated in a $CO_2$ incubator at 37° C. The medium is replaced after 3 to 5 days, respectively, with fresh RPMI 1640 HAT medium, and, depending on the growth of the fused cells, the culture supernatants are tested after approximately 2 weeks for the reactivity thereof with respect to the antigen (My-C) using an ELISA.

EXAMPLE 2

Selection of the Antibody-Producing Clones

All growing clones or the antibodies thereof were tested for reactivity using an enzyme-linked immunosorbent assay (ELISA). The immunosorbent was the immunogen, this being the recombinant cC0C2 domain of the My-C (approximately 2 μg/ml).

Carrying out the ELISA:
1. Coat each of the microtiter plates (Costar, high binding) with 50 μl immunogen solution per well at 4° C. over night;
2. wash the microtiter plates (MTP) 3 times with Tris-buffered saline (TBS), pH 7.4;
3. block the MTP using 200 μl blocking reagent (Boehringer, Mannheim) per well, 1 hour at 37° C.;
4. wash the MTP 3 times with NaCl Tween 20;
5. incubate with culture supernatant of the hybridoma cultures; 50 μl per well, respectively, diluted approximately 1:2 with TBS Tween 20;
6. wash the MTP 3 times with NaCl Tween 20;
7. incubate with anti-mouse Ig antibodies, coupled to peroxidase, 50 μl per well, 1 hour at room temperature;
8. wash the MTP 3 times with NaCl Tween 20;

9. incubate with ABTS solution (100 mg ABTS per 100 ml substrate buffer [citrate, sodium perborate, pH 4.4]), 50 µl per well;
10. measure at 405 nm after an incubation time of 60 minutes at room temperature using a microplate reader (SLT).

EXAMPLE 3

Epitope Mapping for the Monoclonal Antibody 1A4 in the Human Cardiac My-C

The binding site of the monoclonal antibody 1A4 was identified by way of the peptide scanning method. For this purpose, the entire amino acid sequence of the human cC0C2 domain of the My-C that was used for the immunization is divided into a total of 111 overlapping amino acid sequences, each having a length of 15 amino acids. These sequences are synthesized as individual peptides in spots directly on a cellulose membrane. The membrane is incubated with the antibody-containing culture supernatants of the hybridomas, and the binding sites of the antibodies are rendered visible by way of incubation with a peroxidase-coupled anti-mouse Ig antibody. For this purpose, after washing three times with TBS Tween, the membrane is placed between copy film, and then incubated for 3 minutes with the ECL™(enhanced chemiluminescent) detection reagent (Amersham, Braunschweig). An applied film (HYPERFILM ECL™ [RPN 2103H Amersham, Braunschweig]) is thereafter exposed to light, for between 30 seconds and 3 minutes.

The identification of the sequences detected by the antibody takes place by assigning the spots 31 and 32 (FIG. 4) exposed on the film to the 15-mer partial sequences of the immunogen (cC0C2 domain of the My-C) localized in the spots.

Spot 31 121 PAPAAELGESAPSPK 15 1A4 (SEQ ID NO. 36)

Spot 32 125 AELGESAPSPKGSSS 15 1A4 (SEQ ID NO. 37)

The identified central sequence of the two partial sequences is the amino acid sequence—$A_{124}$ -A-E-L-G-E-S-A-P-S-P-K-(SEQ ID NO. 1). This sequence is the detected epitope to which the antibody 1A4 binds in the human My-C.

LITERATURE

1. Cooper A, Timmis A, Skinner J. Assessment of recent onset chest pain or discomfort of suspected cardiac origin: Summary of nice guidance. BMJ. 2010;340:c1118
2. Thygesen K, Alpert J S, Jaffe A S, Simoons M L, Chaitman B R, White H D, Katus H A, Lindahl B, Morrow D A, Clemmensen P M, Johanson P, Hod H, Underwood R, Bax J J, Bonow R O, Pinto F, Gibbons R J, Fox K A, Atar D, Newby L K, Galvani M, Hamm C W, Uretsky B F, Steg P G, Wijns W, Bassand J P, Menasche P, Ravkilde J, Ohman E M, Antman E M, Wallentin L C, Armstrong P W, Januzzi J L, Nieminen M S, Gheorghiade M, Filippatos G, Luepker R V, Fort-mann S P, Rosamond W D, Levy D, Wood D, Smith S C, Hu D, Lopez-Sendon J L, Robertson R M, Weaver D, Tendera M, Bove A A, Parkhomenko A N, Vasilieva E J, Mendis S. Third universal definition of myocardial infarction. Circulation. 2012; 126:2020-2035
3. Gersten R E, Carr S A, Sabatine M. Integration of proteomic-based tools for improved biomarkers of myocardial injury. Clin.Chem. 2010;56:194-201
4. Katus H A, Remppis A, Neumann F J, Scheffold T, Diederich K W, Vinar G, Noe A, Matern G, Kuebler W. Diagnostic efficiency of troponin t measurements in acute myocardial infarction. Circulation. 1991; 83:902-912
5. Morrow D A, Cannon C P, Jesse R L, Newby L K, Ravkilde J, Storrow A B, Wu A H, Christenson R H. National academy of clinical biochemistry laboratory medicine practice guidelines: Clinical characteristics and utilization of biochemical markers in acute coronary syndromes. Circulation. 2007; 115:e356-375
6. Hoeller R, Rubini Gimenez M, Reichlin T, Twerenbold R, Zellweger C, Moehring B, Wildi K, Freese M, Stelzig C, Hartmann B, Stoll M, Mosimann T, Reiter M, Haaf P, Mueller M, Meller B, Hochgruber T, Balmelli C, Sou S M, Murray K, Freidank H, Steuer S, Minners J, Osswald S, Mueller C. Normal presenting levels of high-sensitivity troponin and myocardial infarction. Heart. 2013
7. Baker J O, Reinhold J, Redwood S, Marber MS. Troponins: Redefining their limits. Heart. 2011; 97:447-452
8. Jacquet S, Yin X, Sicard P, Clark J, Kanaganayagam G S, Mayr M, Marber M S. Identification of cardiac myosin-binding protein c as a candidate biomarker of myocardial infarction by proteomics analysis. Mol Cell Proteomics. 2009; 8:2687-2699
9. Aye T T, Scholten A, Taouatas N, Varro A, Van Veen T A, Vos M A, Heck A J. Proteome-wide protein concentrations in the human heart. Mol Biosyst. 2010; 6:1917-1927
10. Sadayappan S, de Tombe PP. Cardiac myosin binding protein-c: Redefining its structure and function. Biophys Rev. 2012; 4:93-106
11. Baker J O, Devaraj R, Reinhold J, Kanaganayagam G, Sadayappan S, Gautel M, Redwood S, Marber M. Cardiac myosin-binding protein c as a potential new serum biomarker of myocardial infarction. Circulation. 2010;122: A15438
12. Govindan S, Kuster D W, Lin B, Kahn D J, Jeske W P, Walenga J M, Leya F, Hoppensteadt D, Fareed J, Sadayappan S. Increase in cardiac myosin binding protein-c plasma levels is a sensitive and cardiac-specific biomarker of myocardial infarction. Am J Cardiovasc Dis. 2013; 3:60-70
13. Govindan S, McElligott A, Muthusamy S, Nair N, Barefield D, Martin J L, Gongora E, Greis K D, Luther P K, Winegrad S, Henderson K K, Sadayappan S. Cardiac myosin binding protein-c is a potential diagnostic biomarker for myocardial infarction. J Mol Cell Cardiol. 2012; 52:154-164
14. Liebetrau C, Mollmann H, Nef H, Szardien S, Rixe J, Troidl C, Willmer M, Hoffmann J, Weber M, Rolf A, Hamm C. Release kinetics of cardiac biomarkers in patients undergoing trans-coronary ablation of septal hypertrophy. Clin Chem. 2012; 58:1049-1054
15. Khler, G., Milstein, C, Nature, 1975, 256 (5517): 495-497;
16. Kearney, J. F., Radbruch, A., Liesegang, B., Rajewsky, K., J. Immunol., 1979, 123(4):1548-50;
17. Galfre, G., Milstein, C, Methods Enzymol., 1981, 73(Pt B): 3-46
18. Geysen, H. M., Rodda, S. J., Mason, T. J., Tribbick, G., Schoofs, P. G., J. Immunol. Methods, 1987, 102(2): 259-274

The invention claimed is:

1. A hybridoma cell line DSM ACC3224, producing a murine monoclonal antibody anti-My-C-cC0C2-259-1A4 against human cardiac myosin-binding protein c (My-C).

2. The hybridoma cell line according to claim 1, wherein the hybridoma cell line is obtained by fusing spleen lymphoblasts of a mouse immunized with myeloma cells against the cC0C2 domains of My-C, and by producing a monoclonal antibody against a cardiac epitope in the My-C.

3. The hybridoma cell line according to claim 1, wherein the spleen lymphoblasts are those of BALB/c mice, and the myeloma cells are those of the line P3X63Ag8.653.

4. The hybridoma cell line according to claim 1, wherein the monoclonal antibody is specific to an epitope having the sequence AAELGESAPSPK (SEQ ID NO. 1), in the region of the amino acids A124 to K134 of the sequence of the human cardiac My-C.

5. A monoclonal antibody, anti-My-C-cC0C2-259-IA4, wherein the monoclonal antibody identifies and binds an epitope having the sequence according to SE Q ID NO: 1, in the region of the amino acids A124 to K134 of the sequence of the human cardiac My-C; and wherein the monoclonal antibody is produced by the hybridoma cell line DSM ACC3224 of claim 1.

6. A method for producing murine monoclonal antibody according to claim 5, comprising cultivating a myeloma cell line DSM ACC3224, producing a murine monoclonal antibody anti-My-C-cC0C2-259-1A4 against human cardiac myosin-binding protein c (My-C), and isolating the monoclonal antibodies thereby produced.

7. An ELISA method for determining concentration of My-C in a body fluid, and, thus, early diagnosis of myocardial infarctions, said method comprising a step of contacting the monoclonal antibody according to claim 5 with a sample of the body fluid, wherein the monoclonal antibody is a catcher antibody or a detector antibody.

8. An analytical method, comprising a step of contacting the monoclonal antibody according to claim 5 with a sample to be analyzed, wherein the monoclonal antibody is a reagent.

9. The analytical method according to claim 8, wherein the analytical method is an immunoblot.

10. The analytical method according to claim 8, wherein the analytical method is immunohistochemistry.

* * * * *

UNITED STATES PATENT AND TRADEMARK OFFICE
CERTIFICATE OF CORRECTION

PATENT NO. : 10,017,745 B2
APPLICATION NO. : 15/114670
DATED : July 10, 2018
INVENTOR(S) : Weber and Medek Page 1 of 1

It is certified that error appears in the above-identified patent and that said Letters Patent is hereby corrected as shown below:

In the Specification

In Column 3, Line 21, delete "A124--A-E-L-G-E-S-A-P-S-P-K" and replace it with --A-E-L-G-E-S-A-P-S-P-K--

In Column 5, Lines 46-47, delete "A124--A-E-L-G-E-S-A-P-S-P-K" and replace it with --A-E-L-G-E-S-A-P-S-P-K--

In the Sequence Listing

In Column 7, Line 3, delete "<211> LENGTH: 12" and replace it with --<211> LENGTH: 11--

In Column 7, Line 7, delete "Ala Ala Glu Leu Gly Glu Ser Ala Pro Ser Pro Lys" and replace it with --Ala Glu Leu Gly Glu Ser Ala Pro Ser Pro Lys--

In the Claims

In Column 21, Line 44, delete "AAELGESAPSPK" and replace it with --AELGESAPSPK--

In Column 21, Line 45, delete "A124 to K134" and replace it with --A125 to K135--

In Column 21, Line 50, replace "A124 to K134" with --A125 to K135--

Signed and Sealed this
Seventeenth Day of November, 2020

Andrei Iancu
*Director of the United States Patent and Trademark Office*